US00PP15678P2

(12) United States Plant Patent
Trees

(10) Patent No.: US PP15,678 P2
(45) Date of Patent: Mar. 15, 2005

(54) ***GERANIUM* PLANT NAMED 'BALDESBRILA'**

(50) Latin Name: *Pelargonium×hortorum*
Varietal Denomination: Baldesbrila

(75) Inventor: Scott C. Trees, Shell Beach, CA (US)

(73) Assignee: Ball Horticultural Company, West Chicago, IL (US)

( * ) Notice: Subject to any disclaimer, the term of this patent is extended or adjusted under 35 U.S.C. 154(b) by 3 days.

(21) Appl. No.: 10/741,485

(22) Filed: Dec. 19, 2003

(51) Int. Cl.[7] ..... A01H 5/00
(52) U.S. Cl. ..... Plt./329
(58) Field of Search ..... Plt./329, 325

*Primary Examiner*—Kent Bell
*Assistant Examiner*—Louanne Krawczewicz Myers
(74) *Attorney, Agent, or Firm*—Wood, Phillips, Katz, Clark & Mortimer

(57) ABSTRACT

A new and distinct cultivar of *Geranium* plant named 'Baldesbrila', characterized by its semi-double bright lavender-colored flowers, medium green-colored foliage and moderate, upright and mounded growth habit.

1 Drawing Sheet

Latin name of genus and species of plant claimed: *Pelargonium×hortorum.*
Variety denomination: 'Baldesbrila'.

BACKGROUND OF THE INVENTION

The present invention relates to a new and distinct cultivar of *Geranium* plant botanically known as *Pelargonium× hortorum* and hereinafter referred to by the cultivar name 'Baldesbrila'.

The new cultivar originated in a controlled breeding program in Arroyo Grande, Calif. during 2000. The purpose of the breeding program was the creation of *Geranium* plants with vigorous upright mounded growth habits, dark green foliage, and unique flower colors.

The female parent of 'Baldesbrila' was the proprietary *Pelargonium×hortorum* selection designated 'BFP-1757-1' (not patented). The male parent of 'Baldesbrila' was the proprietary *Pelargonium×hortorum* selection designated 'BFP-867-23' (not patented). The new *Geranium* was discovered and selected by the inventor as a single flowering plant from within the progeny of the above stated cross-pollination during March 2001 at Arroyo Grande, Calif. and was initially designated '2620-6'.

Asexual reproduction of the new cultivar by terminal stem cuttings taken since 2001 at Arroyo Grande, Calif. and West Chicago, Ill., has demonstrated that the new cultivar reproduces true to type with all characteristics, as herein described, firmly fixed and retained through successive generations of such asexual propagation.

SUMMARY OF THE INVENTION

The new cultivar has not been observed under all possible environmental conditions to date. Accordingly, it is possible that the phenotype may vary somewhat with variations in the environment, such as temperature, light intensity, and day length, without, however, any variance in genotype.

It was repeatedly found that the cultivar of the present invention:

1. Forms semi-double bright lavender-colored flowers,
2. Forms medium green-colored foliage, and
3. Exhibits a moderate, upright and mounded growth habit.

Plants of the new cultivar differ from plants of the female parent primarily in flower form, flower color, and foliage color. Plants of the new cultivar differ from plants of the male parent primarily in flower color and foliage color.

Of the many commercially available *Geranium* cultivars known to the inventor, the most similar in comparison to 'Baldesbrila' is 'Baldesvio' (U.S. Plant Pat. No. 11,676). However, in side-by-side comparisons, plants of 'Baldesbrila' differ from plants of 'Baldesvio' in the following characteristics:

1. Plants of 'Baldesbrila' exhibit lighter flower color than plants of 'Baldesvio', and
2. Plants of 'Baldesbrila' have leaves with a more distinct zonation than plants of 'Baldesvio'.

BRIEF DESCRIPTION OF THE PHOTOGRAPHS

The accompanying photographs show as nearly true as it is reasonably possible to make the same in color illustrations of this type, typical flower and foliage characteristics of the new cultivar. Colors in the photographs differ slightly from the color values cited in the detailed description, which accurately describes the colors of 'Baldesbrila'. The plants were grown for 8 weeks in a greenhouse at West Chicago, Ill.

DETAILED BOTANICAL DESCRIPTION

Figure 1:
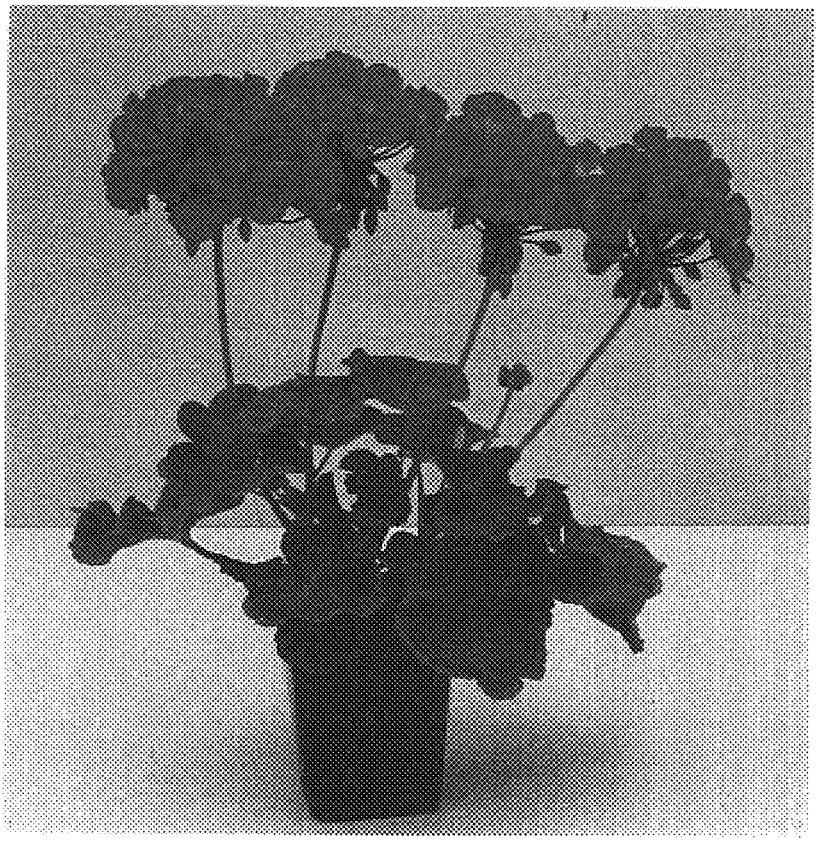
FIG. 1 illustrates a side view of the overall growth and flowering habit of 'Baldesbrila'.
Figure 2:
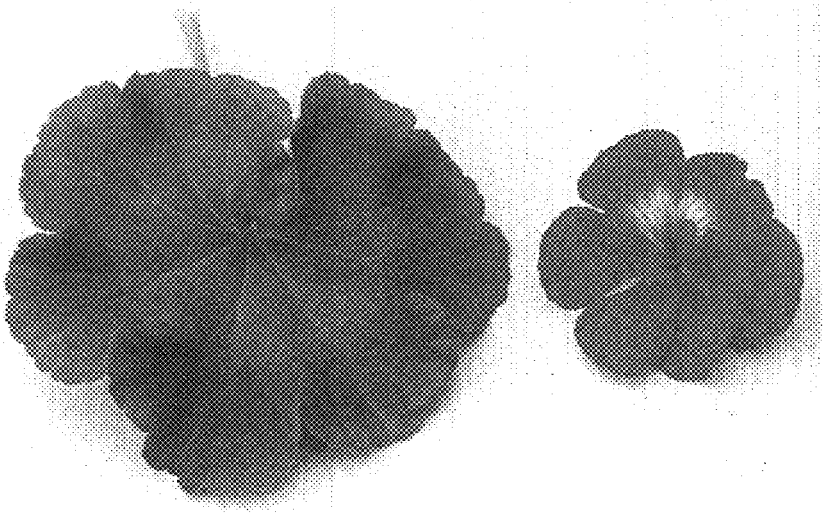
FIG. 2 illustrates a close-up view of a single flower and leaf of 'Baldesbrila'.

The chart used in the identification of colors described herein is the R.H.S. Colour Chart of The Royal Horticultural Society, London, England, 2001 edition, except where general color terms of ordinary significance are used. The color values were determined on Jul. 30, 2003 in West Chicago, Ill. The readings were taken between 10:00 and 11:45 a.m. under natural light conditions.

The plants used for the following measurements and descriptions were produced from cuttings taken from stock plants and grown in a double polycarbonate-covered greenhouse under conditions comparable to those used in commercial practice. The plants were grown in 10 cm pots for 8 weeks utilizing a soilless growth medium. Greenhouse temperatures were maintained at approximately 65°–70° F. (18°–21° C.) during the day and approximately 60°–65° F. (15°–18° C.) during the night. Greenhouse light levels of 4,000–6,000 footcandles were maintained during the day. Plants were pinched at three weeks after planting.

Botanical classification: *Pelargonium×hortorum* cultivar 'Baldesbrila'.

Parentage:

*Female parent*.—Proprietary *pelargonium×hortorum* selection designated 'BFP-1757-1' (not patented).

*Male parent*.—Proprietary *pelargonium×hortorum* selection designated BFP-'867-23' (not patented).

Propagation:

*Type cutting*.—Terminal stem.

*Time to initiate roots*.—Approximately 10 to 14 days.

*Time to develop roots*.—Approximately 21 to 28 days.

*Root description*.—Fibrous.

*Rooting habit*.—Freely branching.

Plant description:

*General appearance and growth habit*.—Upright mounded and vigorous.

*Height above pot*.—Without inflorescences: Approximately 14.7 cm. Including inflorescences: Approximately 25.4 cm.

*Width/area of spread*.—Approximately 24.7 cm.

*Branching habit*.—Freely basal branching. Approximately 3 branches per plant. Pinching 14 to 21 days after transplanting helps to improve basal branching.

*Branch description*.—Length: Approximately 7.3 cm. Diameter: Approximately 8 mm. Color: Closest to 146A. Texture: Hirsute. Internode length at center of branch: Approximately 1.3 cm.

*Foliage description*.—Form: Mature foliage is simple. Arrangement: Opposite. Number of leaves per lateral branch: Approximately 10. Shape: Reniform. Margin: Crenate. Apex: Rounded. Base: Cordate. Venation pattern: Palmate. Upper surface texture: Densely pubescent. Lower surface texture: Moderately pubescent with dense pubescence along veins. Color of mature foliage: Upper surface: 146B with veins of 145A and faint zone of 146A, 2 cm wide from margin. Lower surface: 146B with veins of 145A. Size: Mature leaf length: Approximately 4.7 cm. Mature leaf width: Approximately 8.1 cm. Petiole length: Approximately 6.8 cm. Petiole diameter: Approximately 2.3 mm. Petiole Texture: Pubescent. Petiole color: 146B.

Flowering description:

*Outdoor flowering habit*.—'Baldesbrila' is freely flowering under outdoor growing conditions with substantially continuous blooming from spring through fall.

*Time of first flower*.—Approximately 8 weeks after planting of rooted cutting.

*Lastingness of individual bloom*.—Approximately 5–7 days.

Inflorescence description:

*Type*.—Hemispherical umbel. Position: Above foliage. Number of open umbels at any one time: One. Number of developing umbels at any one time: Three. Umbel diameter: Approximately 9.9 cm. Umbel height/depth: Approximately 6.4 cm. Number of flowers per umbel: Approximately 18.

*Peduncle*.—Strong, erect. Length: Approximately 15.6 cm. Diameter: Approximately 4 mm. Texture: Pubescent. Color: Closest to 146A.

Flower description:

*Bud just before opening*.—Shape: Elliptic. Length: Approximately 1 cm. Diameter: Approximately 6 mm. Petal color: N66D. Sepal color: 144B.

*Corolla*.—Form: Semi-double. Shape: Round, slightly cupped. Diameter/Width: Approximately 4.7 cm. Depth: Approximately 2 cm. Fragrance: None. Persistent.

*Petals/petaloids*.—Quantity: Approximately 7 petals and 2 petaloids per flower. Arrangement: Imbricate. Shape: Obovate. Apex: Obtuse. Base: Attenuate. Margin: Entire. Texture of upper and lower surface: Glabrous. Upper petal length: Approximately 2.3 cm. Upper petal width: Approximately 1.8 cm. Lower petal length: Approximately 2.1 cm. Lower petal width: Approximately 1.8 cm. Color of all petals: Fully opened, upper surface: Closest to N74A. Bases of upper petals are N155C with venation of N74A. Color of all petals: Fully opened, lower surface: Closest to 68A with N74A at margin and venation at base of N74A. Petaloid shape: Irregular. Petaloid length: 1.5 cm. Petaloid color (upper and lower surfaces): Closest to N74A.

*Pedicel*.—Strength: Strong. Angle: Erect. Length: Approximately 2.8 cm. Diameter: Approximately 1 mm. Texture: Soft, short dense hairs. Color: 144B with heavy overlay of 183B.

*Sepals*.—Quantity per flower: 5. Shape: Elliptic. Tip: Acuminate. Base: Truncate. Margin: Entire. Length of largest sepal: 8 mm. Width of largest sepal: 4 mm. Length of smallest sepal: 8 mm. Width of smallest sepal: 2 mm. Texture: Upper surface (inside): Glabrous. Lower surface (outside): Puberulent. Color: Upper and lower surface: 144B.

*Reproductive organs*.—Androecium: Stamen number: Approximately 11 per flower. Filament quantity: Approximately 11. Filament color: N155B. Anther quantity: Approximately 11. Anther length: Approximately 1.5 mm. Anther color: 64A. Pollen amount: Moderate. Pollen color 169B. Gynoecium: Pistil quantity: One per flower. Pistil length: Approximately 1 cm. Stigma shape: 5 pointed star. Stigma length: 2.5 mm. Stigma color: 63A. Style length: 2.5 mm. Style color: 63A. Ovary length: 5 mm. Ovary diameter: 2 mm. Ovary texture: Sericeous. Ovary color: 144A.

Seed and fruit production: Neither seed nor fruit production has been observed.

Disease and pest resistance: Resistance to diseases and pests common to *Geraniums* has not been observed.

Hardiness zone: 'Baldesbrila' is presumably hardy in zones nine (9) and above.

What is claimed is:

1. A new and distinct cultivar of *Geranium* plant named 'Baldesbrila' substantially, as herein shown and described, which:

1. Forms semi-double bright lavender-colored flowers,
2. Forms medium green-colored foliage, and
3. Exhibits a moderate, upright and mounded growth habit.

* * * * *